(12) United States Patent
Baron et al.

(10) Patent No.: US 8,371,847 B2
(45) Date of Patent: Feb. 12, 2013

(54) METHOD FOR DESIGNING ORTHODONTIC APPARATUS

(76) Inventors: Pascal Baron, Colomiers (FR); Christophe Gualano, Blagnac (FR); Laurent Sempe, Toulouse (FR)

( * ) Notice: Subject to any disclaimer, the term of this patent is extended or adjusted under 35 U.S.C. 154(b) by 131 days.

(21) Appl. No.: 12/937,588

(22) PCT Filed: Apr. 3, 2009

(86) PCT No.: PCT/EP2009/054006
§ 371 (c)(1),
(2), (4) Date: Dec. 15, 2010

(87) PCT Pub. No.: WO2009/127536
PCT Pub. Date: Oct. 22, 2009

(65) Prior Publication Data
US 2011/0086322 A1   Apr. 14, 2011

(30) Foreign Application Priority Data
Apr. 14, 2008   (FR) ...................... 08 52493

(51) Int. Cl.
*A61C 7/00* (2006.01)

(52) U.S. Cl. ............................. 433/24; 433/8

(58) Field of Classification Search ............. 433/8, 9, 433/24
See application file for complete search history.

(56) References Cited

U.S. PATENT DOCUMENTS

| 5,395,238 | A | | 3/1995 | Andreiko et al. |
| 5,431,562 | A | * | 7/1995 | Andreiko et al. ............... 433/24 |
| 5,454,717 | A | * | 10/1995 | Andreiko et al. ............... 433/24 |
| 6,015,289 | A | * | 1/2000 | Andreiko et al. ............... 433/3 |
| 6,736,638 | B1 | * | 5/2004 | Sachdeva et al. ............... 433/24 |
| 7,811,087 | B2 | * | 10/2010 | Wiechmann et al. ............. 433/9 |
| 7,850,451 | B2 | * | 12/2010 | Wiechmann et al. ........... 433/24 |
| 8,057,226 | B2 | * | 11/2011 | Wiechmann et al. ........... 433/16 |
| 2002/0025503 | A1 | | 2/2002 | Chapoulaud et al. |
| 2006/0147872 | A1 | | 7/2006 | Andreiko |
| 2007/0015104 | A1 | | 1/2007 | Wiechmann et al. |

FOREIGN PATENT DOCUMENTS

| EP | 1702582 A2 | 9/2006 |
| WO | 0180761 A2 | 11/2001 |

OTHER PUBLICATIONS

International Search Report, dated Oct. 9, 2009, from corresponding PCT application.

* cited by examiner

*Primary Examiner* — Ralph Lewis
(74) *Attorney, Agent, or Firm* — Young & Thompson

(57) ABSTRACT

A method of producing a customized orthodontic appliance (1), including brackets (12) fixed to teeth (13) of a dental arch of a patient and an orthodontic archwire (11). Each bracket (12) is fixed to a surface of a tooth (13) of the dental arch by a bracket bonding pad (121) of the bracket, and the orthodontic archwire (11) is fixed to the brackets in a housing (123) of a bracket body (122) of each bracket. The bracket is produced with a blank (50) having at least two volumes (51, 52), one volume representative of an envelope volume of a bracket bounding pad and an envelope volume of a bracket body.

15 Claims, 4 Drawing Sheets

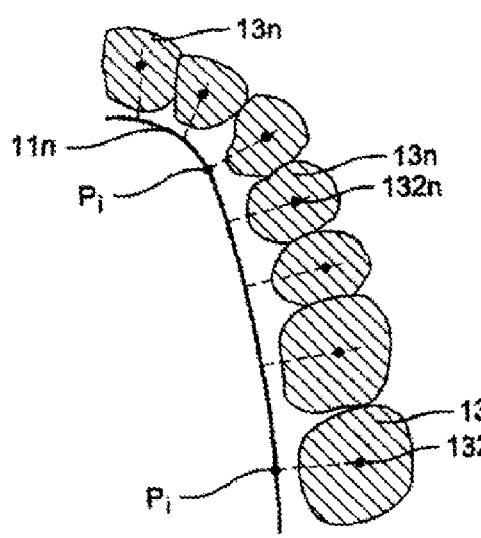
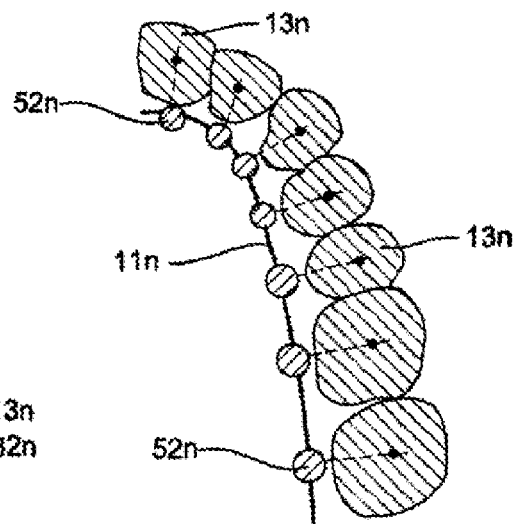
Fig. 5a          Fig. 5b
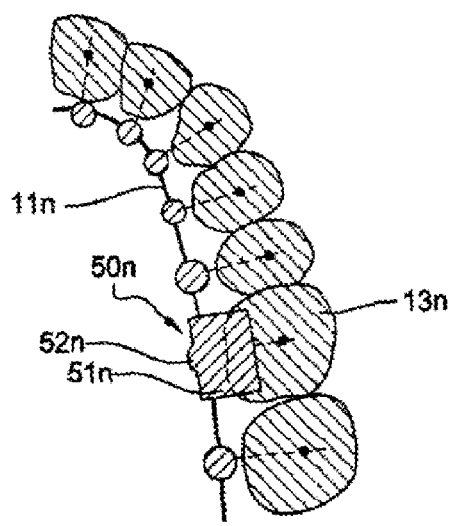
Fig. 6a

METHOD FOR DESIGNING ORTHODONTIC APPARATUS

BACKGROUND OF THE INVENTION

1. Field of the Invention

The present invention belongs to the field of orthodontics. More specifically, the invention relates to a method of designing an orthodontic appliance, the said bracket being tailored to each tooth of a patient thus allowing the orthodontic appliance to be customized.

2. Description of the Related Art

Orthodontics is a medical specialty used to correct the positions of poorly positioned teeth of a dental system or when the jaw has been malformed, in order to recover a functional and aesthetic dentition.

Orthodontic treatment consists in using an orthodontic appliance to apply force to one or more teeth of a dental system/dentition so as to cause them gradually to move into a determined position in order ultimately to achieve a better tooth alignment.

The orthodontic appliance is generally formed by brackets securely fastened to the teeth and an orthodontic archwire that applies forces to the teeth via the brackets. In the current format, the orthodontic archwire is usually held in place by a housing in each of the brackets. A bracket comprises a bracket bonding pad and a bracket body comprising the housing. The bracket is attached to a surface of a tooth via the bracket bonding pad. The orthodontic archwire extends between the brackets over adjacent teeth and applies a force to each tooth in order to move the teeth individually into their determined positions.

Each bracket of the orthodontic appliance is fixed to the said bracket on a surface of the corresponding tooth which lies on the lip side, and is known as the vestibular (or sometimes labial) surface, to make it easier to attach the brackets and the orthodontic archwire and to make it easier to adjust the said orthodontic archwire.

Increasingly often, for mainly aesthetic reasons, orthodontic appliances have been developed in which each bracket is fixed to a surface of the corresponding tooth that lies inside the mouth, on the palate side, of a patient, known as the lingual surface.

One concept generally employed in orthodontics relies on configuring the orthodontic archwire as a straight archwire. What a straight archwire is, is an archwire substantially in the shape of a flat U, a semi-elliptical shape or a parabolic shape, that is to say a flat regular curve positioned with respect to the dental arch parallel to the occlusal plane.

A straight archwire is not specific to a patient's dental arch and has a simple shape that can be produced easily and on an industrial scale, and therefore at low cost.

In the case of a dental arch that requires orthodontic treatment, a preformed straight archwire that has the desired shape of the dental arch at the end of treatment is used. When a predefined straight archwire is positioned on an orthodontic appliance in position on a dental arch, the said straight archwire is partially deformed, within the elastic limits of the material of which the straight archwire is made, as they are inserted into the slot of each bracket. When the treatment is finished, the straight archwire will have returned to its initial shape because the teeth will have been moved under the effect of the forces exerted by the prestressed orthodontic archwire. In practice, a straight archwire has a rectangular, square or round cross section and its curvature is modified as the treatment progresses.

In a configuration such as this, because the orthodontic archwire is not specifically designed for a patient's dental arch, it is the brackets which are specially tailored to each one of a patient's teeth.

In order to design an orthodontic appliance tailored to each of a patient's teeth, one known method of designing and producing brackets is to produce an integral (bracket bonding pad and bracket body) bracket from numerical models of separate elements, one element representative of the bracket bonding pad and one element representative of the bracket body, and then numerically assemble them.

In order to achieve the production of a bracket, the method includes the steps of:

numerically representing the dentition of the patient, formulating the bracket bonding pad of a bracket on the lingual face of the relevant tooth, in numerical form, selecting a numerical representation of a bracket body from a database, positioning the numerical representation of the selected numerical bracket body on the bracket bonding pad of the bracket.

The bracket thus designed is a numerical object corresponding to the merger of a number of three-dimensional objects (bracket bonding pad and bracket body) designed to suit, and containing customized designs for each of the patient's teeth.

The numerical object is then exported in the form of numerical files to a machine tool or the like intended to produce the bracket from a biocompatible material in accordance with the shape thus defined.

In this method of manufacturing a bracket, only the bracket bonding pad is designed numerically from the surface of the patient's tooth, the bracket body being taken from a database and firmly attached to the bracket bonding pad later.

BRIEF SUMMARY OF THE INVENTION

The present invention proposes a method of producing a customized orthodontic appliance. An orthodontic appliance comprises:

brackets fixed to teeth of a dental arch of a patient, each bracket being fixed to a surface of a tooth of the dental arch by a bracket bonding pad of the said bracket, an orthodontic archwire fixed to the said brackets in a housing of a bracket body of each bracket.

The method according to the invention includes a step of constructing a numerical representation of each bracket from a numerical representation of the desired end-of-treatment dental arch, known as the dental arch final numerical representation. According to the method, the step of constructing the numerical representation of each bracket comprises the steps of:

a—positioning a numerical representation of the orthodontic archwire with respect to the dental arch final numerical representation, then b—for each tooth of the dental arch final numerical representation, positioning a numerical representation of a volume representative of an envelope volume of a bracket body, known as the second volume, of a bracket blank such that it interferes with the orthodontic archwire and in close proximity to the relevant tooth, and c—for each tooth of the dental arch final numerical representation, positioning a numerical representation of a volume representative of an envelope volume of a bracket bonding pad, known as the first volume, of the bracket blank such that it interferes with the second volume and with the volume of the relevant tooth, then, d—determining, for each tooth in the first volume and in the second volume, volumetric exclusion zones, which volumetric exclusion zones contain all of the volumes that interfere with the tooth for the first volume and all of the volumes that interfere with the orthodontic archwire for the second volume.

The numerical representation of the bracket of one tooth is then determined by the volume of the bracket blank minus the volumetric exclusion zones.

For preference, in order to minimize a thickness of the bracket, the volumetric exclusion zones of the first volume are defined in such a way as to determine a substantially constant thickness of the numerical representation of the bracket bonding pad.

Advantageously, the blank is chosen from a database comprising at least two models of numerical representation of blanks and is chosen in relation to the shape of the relevant tooth so as to minimize the volume of the exclusion zones while at the same time keeping a sufficient aerial contact between a bearing surface of the bracket bonding pad and the surface of the tooth.

In order to implement step a) of the method, the numerical representation of the orthodontic archwire is positioned in such a way that a distance d, for each tooth of the dental arch final numerical representation, between the numerical representation of the orthodontic archwire and the surface of each tooth is greater than a minimum distance $d_{min}$ that corresponds to a minimum thickness of the numerical representation of the brackets at their bracket bodies.

In one embodiment of step b) of the method, for each tooth of the dental arch final numerical representation, the numerical representation of the second volume is positioned in such a way that a reference point of the said second volume corresponds to a point of intersection between the numerical representation of the orthodontic archwire and an orthogonal projection of a centre of the relevant tooth.

In order for the orthodontic archwire to be able to slide naturally along the dental arch in the housings in the brackets as the teeth of the said dental arch move, housings are produced, for certain sectors of the dental arch, with a cross section appreciably larger than a cross section of the said orthodontic archwire.

For preference, the method is described in an application in which the orthodontic archwire is a flat orthodontic archwire because the forces applied by such flat archwires are those best suited both to the buccal physiology and to standardization of the treatment.

Without implying any restriction, the method is implemented using numerical representations of brackets positioned on either lingual or vestibular surfaces of the teeth of the dental arch final numerical representation.

Depending on the tooth considered, for example in the case of the incisors or the canines, the exclusion zones of the second volume determine a housing in the form of an open slot in the numerical representation of the bracket body to accommodate the numerical representation of the orthodontic archwire and, if appropriate, a numerical representation of orthodontic archwire self-ligating means. In the case of the terminal teeth in the dental arch of relevance to the orthodontic appliance, the exclusion zones of the second volume determine a housing in the form of a tube in the numerical representation of the bracket body to accommodate the numerical representation of the orthodontic archwire.

In one particular embodiment of the method, the method includes an additional step of determining volumetric exclusion zones in a numerical representation of at least one volume representative of an envelope volume of an ancillary accessory, known as a third volume, of the bracket blank, then a step of subtracting the said volumetric exclusion zones from the blank in order to produce the ancillary accessory, such as a hook or a button for example.

For preference, the final numerical representation of the dental arch desired at the end of the treatment of the patient is produced from a numerical representation of the dental arch of the patient prior to treatment.

Once the construction step has been completed, the brackets are produced from a biocompatible material, for example by machining, in accordance with the numerical representations.

The invention also relates to a blank for the manufacture of a bracket of an orthodontic appliance, the said bracket comprising a bracket bonding pad, closely applied to a surface of a patient's tooth, and a bracket body comprising a housing to accommodate an orthodontic archwire, the said blank comprising at least two imbricated volumes constituting an envelope of at least two elements that are to be produced, one volume representative of an envelope volume of the bracket bonding pad, known as the first volume, and one volume representative of an envelope volume of a bracket body, known as the second volume.

In a preferred embodiment, the second volume is substantially spherical and located on the said blank on an opposite side of the first volume to a side situated against the tooth.

In one shape example, in the lingual technique, the first volume is a convex body on the tooth side, for example in the case of the canines or incisors, and is a concave body on the tooth side, for example in the case of the premolars or molars.

BRIEF DESCRIPTION OF THE DRAWINGS

A detailed description of the invention is given with reference to the figures which depict:

FIGS. 5a, 5b: an example of the various phases of the third step of the method, illustrating the numerical positioning of a second volume, representative of a bracket body of the bracket, on each tooth, for a cross section of a dental arch in a plane of the orthodontic archwire, FIG. 6a: an illustration of the numerical positioning, on a tooth, of a blank with respect to the numerical representation of the orthodontic archwire and such that it interferes with the volume of the tooth, according to a fourth step of the method, for a cross section of a dental arch in a plane of the orthodontic archwire.

DETAILED DESCRIPTION OF THE PREFERRED EMBODIMENTS

Figure 1:
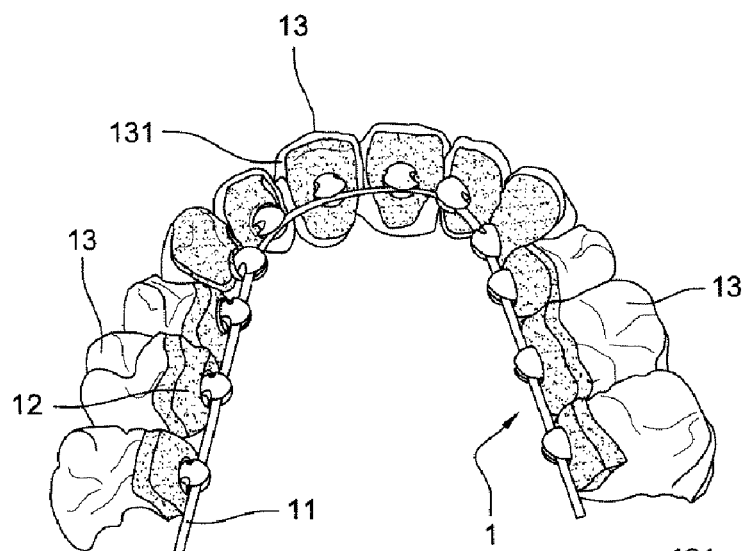
FIG. 1: a view, from the inside of the mouth, of a lingual orthodontic appliance on a dental arch of a patient.

An orthodontic appliance 1, designed for a dental arch, to correct defective positioning of the teeth of a dental system, comprises, as illustrated in FIG. 1, brackets 12, individually fixed to one tooth 13 each, and an orthodontic archwire 11 held in the brackets 12.

The example of an orthodontic appliance is illustrated and described in detail for brackets 12 positioned on surfaces of the teeth 13 that are located on the inside of the mouth, on the palate side, of a patient, known as the lingual surfaces 131. However, this choice is non-limiting and the brackets of the orthodontic appliance could equally be positioned on tooth surfaces situated on the lip side, and on the opposite side to said lingual surfaces, known as the vestibular surfaces.

A dental arch comprises various types of teeth, specifically incisors, canines, premolars and molars.

The orthodontic archwire is a preformed archwire, advantageously a flat archwire, that is to say an archwire situated substantially in one plane, and which has, in a relaxed (that is to say unstressed) position, the shape obtained when the desired shape of the dental arch at the end of treatment is obtained.

The exemplary embodiment of the invention is described in detail for a flat archwire.

The flat archwire is substantially U-shaped or semi-elliptical or parabolical, substantially parallel to the occlusal plane, and, for example, has a uniform flat curve, substantially level with the incisors and the canines, and two substantially straight lines extending from each end of the curve substantially level with the premolars and the molars so that it more or less represents the shape of a dental arch on the side on which the orthodontic archwire is fitted.

The flat orthodontic archwire has a variable cross section, such as, for example, a rectangular, square, circular or elliptical cross section. For the purposes of the illustrations, a rectangular cross section has been adopted.

Figure 2A:
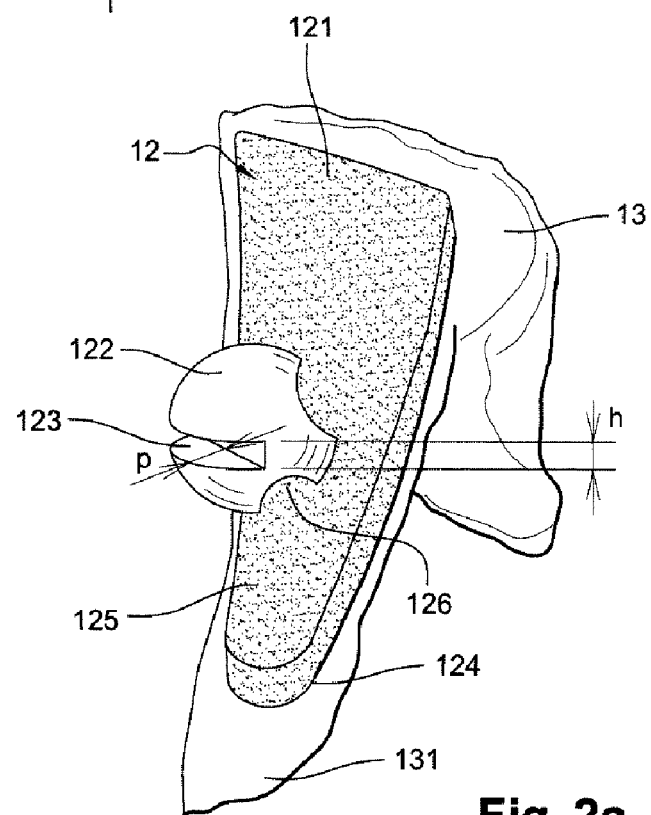
FIG. 2a: a perspective depiction of a bracket according to the invention attached to a surface of a tooth.

A bracket 12 comprises, as illustrated in FIG. 2a, a bracket bonding pad 121, closely following the lingual surface 131 of the tooth 13, and a bracket body 122, firmly attached to the said bracket bonding pad, comprising a housing 123 tailored, in terms of shape and size, to accommodate the orthodontic archwire 11.

The said bracket bonding pad comprises a bearing surface 124, facing the lingual surface 131 of the tooth 13, and which, in inverse relief, has a shape substantially identical to the said lingual surface.

In a known way, the bracket bonding pad 121 is held on the lingual surface 131 of the tooth 13 using an adhesive cement (not depicted).

For preference, the bracket bonding pad has a relatively small thickness that is substantially constant and comprises a surface 125, on the opposite side to the bearing surface 124, that has a shape substantially parallel to the bearing surface 124.

This overall shape of the bracket 12 is particularly well suited to lingual orthodontics because it:
reduces speech problems,
reduces tongue irritation,
is more comfortable for the patient,
is more hygienic,
bonds better, and
allows for better positioning of the bracket for bonding and rebonding.

Each housing 123 has a height h and a depth p and is arranged substantially in a plane of the orthodontic archwire.

In one embodiment, the housing has a height substantially identical to a maximum thickness of the orthodontic archwire.

In another embodiment, the housing has a height appreciably greater than the maximum thickness of the orthodontic archwire so as to accommodate the archwire and, where appropriate, orthodontic archwire self-ligating means (not depicted) inserted into the said housing.

The said orthodontic archwire self-ligating means allow the orthodontic archwire to be kept in place in the housing 123 without the need to resort to additional ligatures. In one exemplary embodiment, the self-ligating means are positioned in the housing 123 and, for example, adopt the form of an anchoring cage. In another exemplary embodiment, the self-ligating means are positioned on the orthodontic archwire.

In one embodiment, a housing has a rectangular cross section substantially, by way of higher value, measuring 0.46×0.64 mm or 0.56×0.71 mm, these dimensions being substantially equivalent to two orthodontic archwire sizes actually in use in the production of orthodontic appliances.

Figure 2B:
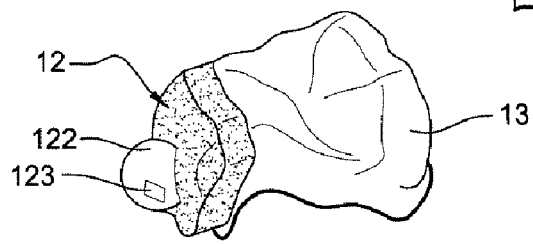
FIG. 2b: a perspective depiction of a bracket according to the invention attached to a surface of a tooth, and comprising a tube.

In a preferred embodiment, the housing 123 adopts the form of an open slot in the plane of the orthodontic archwire for the canines, the premolars and the molars, and adopts the form of a tube for the molars or other terminal teeth, as illustrated in FIGS. 1, 2a and 2b. In this embodiment, only the open slots contain the orthodontic archwire self-ligating means.

In one embodiment, in order to reduce friction and allow the orthodontic archwire 11 to slide naturally along the dental arch in the housings 123 of the brackets as the teeth 13 of the said dental arch move, the orthodontic archwire has a cross section appreciably smaller than a cross section of the housings 123 of the brackets 12 in at least one sector of the dental arch.

In one exemplary embodiment, housings have variable cross sections along sectors of a dental arch in the case of an orthodontic archwire of constant square or rectangular cross section.

In another exemplary embodiment, the orthodontic archwire has a square or rectangular cross section that varies along sectors of dental arch in the case of housings of constant cross section, so as to encourage sliding mechanics during treatment.

This variable cross section of the housing 123 or of the orthodontic archwire 11 also improves control over the position and inclination of the orthodontic archwire in adjusted sections, and mechanical effectiveness in non-adjusted sections.

In order to reconcile better mechanical efficiency with a need for access for tooth-brushing, the housing 123 of the bracket 12 is preferably situated at a cervical limit of the tooth, that is to say as close as possible to the gum line and centred axially on the lingual surface 131 of the tooth 13.

In one embodiment, when the self-ligating means do not exist, the bracket body 122 has secondary slots 126, for example substantially parallel or perpendicular to the slot 123, to accommodate ligatures, for example of the metallic or elastomeric type, to hold the orthodontic archwire 11 in position in the slot of the said bracket body, or auxiliary archwires.

For preference, the bracket body 122 has a rounded or at least blunted shape and has two diametrically opposed secondary slots to accommodate ligatures. For the description, use is made of bracket bodies of hemispherical shapes.

In one embodiment, to allow the treatment of complex disorders, for which the straightening afforded by the bracket 12 is insufficient, the bracket 12 comprises an ancillary accessory (not depicted) in relief, such as, for example, a button, a cleat, a spur or a hook which may be temporary or permanent.

When the ancillary accessory is permanent, the said ancillary accessory is firmly attached to the bracket 12, either at the bracket bonding pad 121 or at the bracket body 122.

When the ancillary accessory is temporary, the bracket body 122 comprises a slit, for example substantially perpendicular to the housing and open-ended, to accept a fastener of the said removable ancillary accessory.

For preference, the bracket 12 is produced from an appropriate material, such as stainless steel for example for its non-corrosive properties, or titanium.

In one particular embodiment, use is made of zirconium oxide which, for such an application, has advantages such as strength and colouring, so that it can be matched to the colour of the teeth.

Figures 3A, 3B:
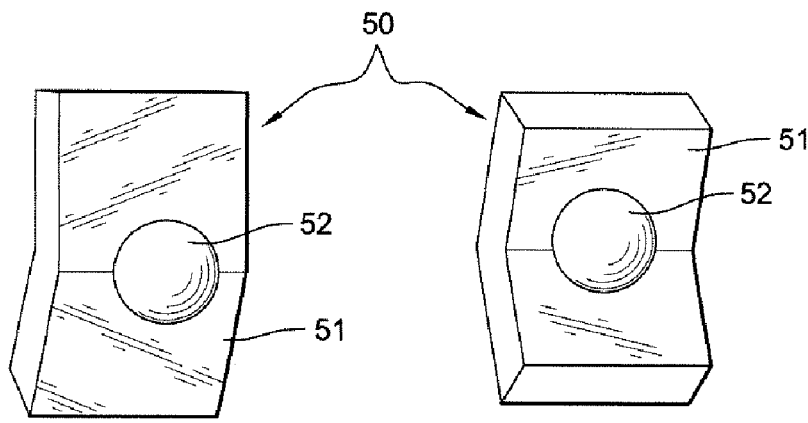
FIG. 3a: a perspective view of a first example of a blank for producing a bracket according to the invention.
FIG. 3b: a perspective view of a second example of a blank for producing a bracket according to the invention.

In order to produce a bracket 12 tailored to the specific shape of a patient's tooth 13, the method according to the invention consists in producing a bracket (bracket bonding pad and bracket body) from the conversion of a blank 50 such as the examples of blanks illustrated in FIGS. 3a and 3b.

The said blank is determined by at least two imbricated volumes 51, 52 which constitute an envelope of the bracket that is to be produced. A first volume 51 is representative of an envelope of the bracket bonding pad 121 of the bracket 12. A second volume 52 is representative of an envelope volume of the bracket body 122 of the bracket 12. Advantageously, the second volume is embodied by a sphere corresponding to an envelope of the bracket body.

In the method, for the step of determining the shape of each bracket, recourse is had to numerical processing of the objects which are themselves represented in numerical form and which can, if need be, be represented graphically as illustrated by the figures. Unless otherwise mentioned and up to such point as the elements of the orthodontic appliance are physically embodied, the description should be understood to mean that each designated object (tooth, orthodontic archwire, bracket, ancillary accessory, etc.) means that numerical representation thereof, whether or not this has been visualized in graphical form, handled by computing means such as a computer. In particular, a suffix n associated with the reference numeral when referring to the figures, means that this is the numerical representation of the designated object.

According to the method, in a first step, a numerical representation of a patient's end-of-treatment dental arch is obtained and stored in a numerical memory. In one method for implementing this first step, the numerical representation is produced in two phases.

A first phase consists in storing a numerical representation, known as the initial numerical representation, of the patient's current dental arch in the numerical memory.

One way of implementing this first phase is, for example, to take an impression of the patient's dentition and then produce a model that will be scanned and converted, using, for example, a software package, into 3D numerical data in order to obtain an initial numerical representation of a dental arch of the current dentition.

Other ways of implementing this first phase are also conceivable, such as, for example, scanning the patient's dentition directly in three dimensions.

A second phase is to obtain a representation, known as the final numerical representation, of the desired end-of-treatment dental arch, from the initial representation.

This final numerical representation contains all of the teeth present at the end of the treatment, in their established arrangements and anatomical relationships.

One way of implementing this second phase is, for example, to use special purpose software that allows the teeth that were incorrectly positioned in the initial representation to be moved into a desired final position, for example 3D graphics software that allows an operator on a workstation fitted with a screen to manipulate each tooth in space.

Figures 4A, 4B:
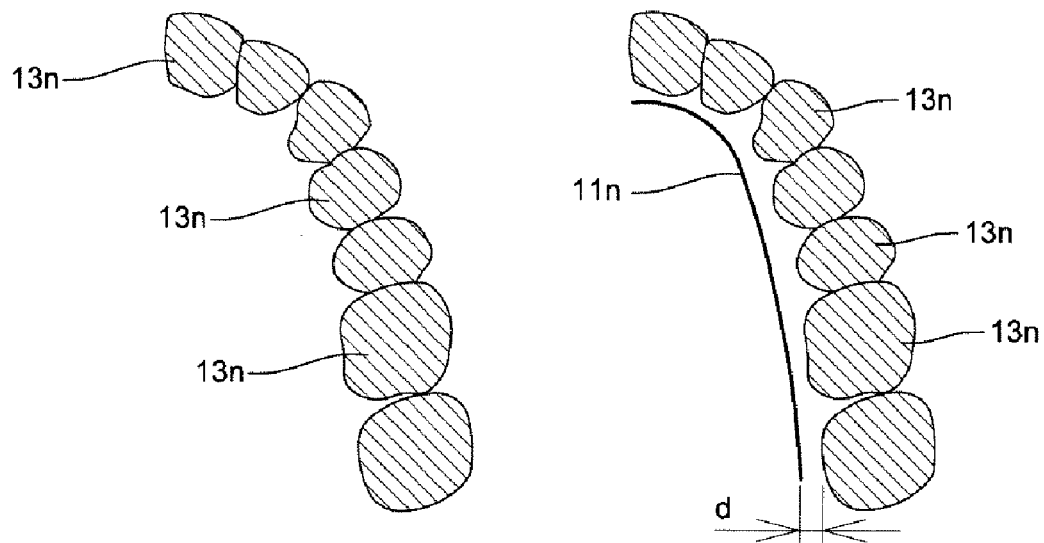
FIG. 4a: an illustration of a numerical representation of a cross section of a dental arch in a plane of the orthodontic archwire.
FIG. 4b: an illustration of a numerical representation of the positioning of an orthodontic archwire for a cross section of a dental arch in a plane of the orthodontic archwire, after a second step of the method.

In a second step of the method, as illustrated in FIGS. 4a and 4b, a flat orthodontic archwire 11n or a line characteristic of the orthodontic archwire, for example an axis, is positioned for the dental arch final numerical representation.

In a first phase, a plane of the orthodontic archwire is determined so that it is secant with the lingual surfaces of the teeth of the dental arch. The position of the said plane, in terms of height and in terms of inclination of the orthodontic archwire, is chosen to suit clinical requirements, and preferably is chosen to lie substantially at a cervical limit of the tooth. FIG. 4a illustrates a cross section through the dental arch considered in the plane of the orthodontic archwire.

In a second phase, the orthodontic archwire 11n is constructed in such a way that the said orthodontic archwire is determined by a continuous flat curve, which is substantially symmetric, of substantially parabolic outline and positioned such that a distance d, for each tooth of the dental arch, between the orthodontic archwire and the lingual surface 131n of each tooth 13n of the dental arch is greater than a minimum distance $d_{min}$ which depends, as appropriate, on the type of tooth considered, and that corresponds to a minimum thickness of the brackets 12n at their bracket body 122n.

In a third step, as illustrated in FIGS. 5a and 5b, spheres 52n representative of the bracket bodies 122n are positioned individually with respect to each lingual surface 131n of the teeth 13n so that the orthodontic archwire 11n passes through them.

In one embodiment, as illustrated in FIG. 5a, in order to determine the position of a sphere 52n, a first phase is, for each tooth, to determine a centre 132n of the tooth 13n.

A second phase is to determine a position on the orthodontic archwire 11n of a point of reference of each sphere 52n. One way of determining the positions on the orthodontic archwire is, for example, to project the centre 132n of each tooth 13n orthogonally onto the orthodontic archwire 11n. The orthogonal projection of the centre of a tooth intersects the orthodontic archwire at a point $p_i$, the suffix i corresponding to the tooth, for example in accordance with the tooth numbering system laid down in the international standards (FIG. 5a).

In a third phase, the sphere 52n is positioned facing the relevant tooth so that a point of reference of the said sphere corresponds to a point $p_i$ (FIG. 5b).

In one exemplary embodiment, the point of reference of a sphere 52n is its centre.

The operation of positioning the spheres 52n is repeated for all those teeth of the dental arch that require a bracket.

For preference, the spheres 52n have a dimension tailored to the dental anatomy. Thus, the spheres may, on the one hand, differ in size within one and the same dental arch for the same patient and, on the other hand, may differ in size for different patients.

For example, for one and the same patient with standard dentition, the said spheres positioned on the lower incisors have a radius of the order of 2 mm and the spheres positioned on the teeth other than the incisors have a radius of the order of 2.5 mm.

Figures 6B, 7:
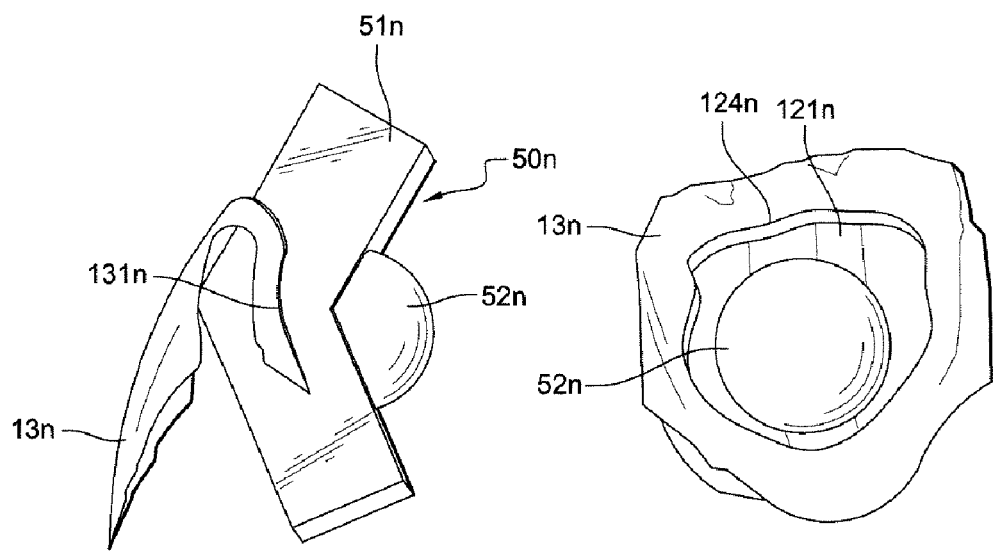
FIG. 6b: a perspective representation, for one tooth, of the numerical positioning of the blank such that it interferes with the volume of the tooth.
FIG. 7: an illustration of one form of bracket bonding pad obtained after the fifth step of the method.

In a fourth step of the method, as illustrated in FIGS. 6a and 6b, a blank 50n, formed on the basis of a first volume 51n associated with the sphere 52n, is positioned on each tooth 13n relative to the predefined orthodontic archwire 11n and such that it interferes with the volume of the tooth 13n.

For each blank 50n, the sphere 52n is positioned in accordance with the position determined beforehand in the previous step.

Each blank 50n is chosen and oriented in such a way that the said first volume 51n is in tune with the anatomy of the relevant tooth, that is to say that the size, shape and orientation of the first volume 51n produces a finished area of intersection that is as great as possible with the lingual surface 131n of the tooth 13n considered.

Advantageously, the blank 50n is chosen from a collection of blanks of different shapes which may advantageously be available in a database comprising various numerical forms of the said blanks 50n, the forms or shapes differing, for example, by having a concave shape or a convex shape, various sizes and various relative positions of the first volume 51n with respect to the sphere 52n.

For preference, the shape of the blank is chosen to suit the natural shape of the teeth and thus improve the later step of fabricating the bracket 12, by limiting the volume of material to be removed from the blank.

In one example of a shape, when the first numerical volumes 51n are preferably intended for the premolars and molars, the said first volumes are concave bodies on the tooth side (FIG. 3a). When the first volumes are preferably intended for the canines and incisors, the said second volumes are convex bodies on the tooth side (FIG. 3b).

In a fifth step of the method, as illustrated in FIG. 7, the volumetric exclusion zones of the first volume 51n of the blank 50n are determined and deleted, for each tooth 13n, so as to produce a numerical representation of a bracket bonding pad 121n.

In one embodiment of this fifth step, the volumetric exclusion zones are determined and deleted in three phases.

A first phase is to eliminate a volumetric exclusion zone of the first volume 51n which is common to the tooth 13n and to the blank 50n.

A second phase is to limit this volumetric exclusion zone to all or part of the lingual surface 131n of the tooth 13n so as to determine a perimeter of the bracket bonding pad 121n at a bearing surface 124n with the lingual surface 131n of the tooth 13n. The bearing surface thus defined conforms to the geometric shape of the lingual surface of the tooth. The said bearing surface is defined by an area of intersection, delimited by a curve that is closed in space, between the first volume 51n and the lingual surface 131n of the tooth 13n. The said area of intersection is defined in such a way that it covers as large an area as possible so as to obtain an interface that best meets the requirements for bonding, such as, for example, stability and retention, and occlusal comfort.

A third phase is to reduce a thickness of the remaining volume of the first volume. A numerical exclusion zone of the remaining volume of the first volume 51n is determined and deleted on a surface of the first volume 51n on the opposite side to the bearing surface 124n with the lingual surface 131n of the tooth 13n so as to limit the thickness of the bracket bonding pad 121n without, however, altering a zone where the first volume 51n meets the sphere 52n.

For preference, in order to reduce the dimensions of the final bracket for improved patient comfort, the bracket bonding pad 121n is produced in such a way that it has a substantially constant thickness which is thus as small as possible while at the same time being able to cope with the forces applied to the bracket.

This fifth step is implemented for each tooth 13n that requires a bracket.

At the end of this fifth step, each bracket 12n consists of the bracket bonding pad 121n firmly secured to the sphere 52n centred on the orthodontic archwire 11n. The bearing surface of the bracket bonding pad is defined in accordance with the geometric shape of the lingual surface of the teeth to make it possible, if necessary, for the final bracket to be repositioned accurately on the said lingual surface during operation of rebonding the said bracket.

Figures 8A, 8B:
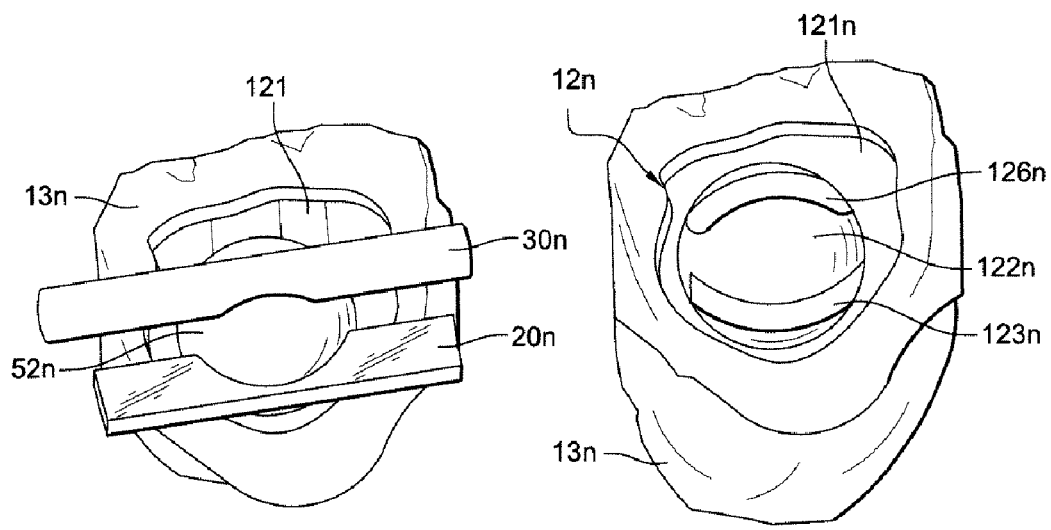
FIGS. 8a, 8b: an example of the various phases of the sixth step of the method, illustrating the production of a numerical representation of the bracket body from the determination and deletion of the volumetric exclusion zones in the second volume.

In a sixth step of the method, as illustrated in FIGS. 8a and 8b, volumetric exclusion zones of the sphere 52n are determined and deleted, for each tooth 13n, so as to produce a numerical representation 122n of a bracket body.

In one embodiment of this sixth step, the volumetric exclusion zones are determined and deleted in two phases.

In a first phase, an exclusion zone is determined to produce a housing 123n to accommodate the orthodontic archwire or orthodontic archwire self-ligating means.

In one embodiment of the first phase, the volumetric exclusion zone representative of the housing 123n is produced in the plane of the orthodontic archwire on a diameter of the sphere 52n in the direction of the orthodontic archwire and forms an open slot on one surface of the sphere 52n so as to design a slot 123n open in the direction of the concave side of the orthodontic archwire. The volumetric exclusion zone is produced in such a way that the slot has minimum heightwise dimensions equal to or greater than the maximum thickness dimensions of the orthodontic archwire in the relevant sector of the dental arch.

One way of determining the volumetric exclusion zone is to design a zone of intersection between the sphere 52n and a first cylinder 20n, for example of substantially rectangular or square cross section, with its largest transverse dimension greater than the diameter of the sphere and its smallest dimension equal to or greater than the maximum thickness dimension of the orthodontic archwire, in the relevant sector of the dental arch.

In another embodiment of the second phase, the volumetric exclusion zone, of a size, in cross section, tailored to the cross-sectional dimensions of the orthodontic archwire, is no longer a slot but a hole. The volumetric exclusion zone is produced in such a way as to have cross-sectional dimensions substantially equal to the cross-sectional dimensions of the orthodontic archwire, in the relevant sector of the dental arch, and is produced in the plane of the orthodontic archwire 11n on a diameter of the sphere 52n. This embodiment is particularly well suited to the back molars.

One way of determining the volumetric exclusion zone representative of the hole is to design a zone of intersection between the sphere and the cylinder (not depicted) passing through the said sphere, with its largest transverse dimension smaller than the diameter of the sphere.

Further, for preference, for certain brackets of the orthodontic appliance, particularly the brackets that have an open slot, at least one volumetric exclusion zone is determined to produce at least one secondary slot 126n to accommodate at least one ligature.

The at least one volumetric exclusion zone representative of at least one secondary slot is produced at the surface of the sphere and is positioned, for example, substantially parallel or perpendicular to the housing 123n.

One way of determining a volumetric exclusion zone is to design a zone of intersection between the sphere 52n and a second cylinder 30, for example of cylindrical cross section, said zone of intersection having the shape and the depth desired for the secondary slot 126n.

For preference, two zones of intersection are produced on the sphere in diametrically opposite positions.

In a second phase, all the volumetric exclusion zones of the sphere are deleted to form the at least one secondary slot 126n and the housing 123n to accommodate the orthodontic archwire.

In one particular embodiment of the method, the sixth step includes an additional phase of determining and deleting a volumetric exclusion zone so as to produce a slit to accommodate a fixing of a temporary ancillary accessory.

The volumetric exclusion zone is produced at the surface of the sphere, for example, positioned preferably at right angles to the slot 123n.

One means for determining the volumetric exclusion zone is to design a zone of intersection between the sphere 52n and a third tube (not depicted), for example of rectangular or square or circular cross section. The volumetric exclusion zone corresponding to the zone of intersection of the sphere and of the third tube is then deleted.

On completion of this sixth step, as illustrated in FIG. 8b, the numerical representation 12n of the bracket thus designed is a three-dimensional numerical object comprising a bracket bonding pad 121n and a bracket body 122n, produced to meet the customized requirements for each of the patient's teeth in the context of a protocol for reconfiguring a dental arch of the patient.

There is no set order in which to perform steps five and six and, according to the method, these steps may be carried out in the opposite order to the order described or may be carried out simultaneously without thereby changing the outcome of the said steps.

For one particular embodiment, when the blank 50n comprises a third volume (not depicted) representative of a permanent ancillary accessory secured to the bracket, the method comprises an additional step of determining and of deleting volumetric exclusion zones of the third volume in order to design the final shape of the ancillary accessory.

This additional step may be carried out between the step of determining the exclusion zones of the first volume and the step of determining the exclusion zones of the second volume or after the step of determining the exclusion zones of the second volume.

The seventh step consists in physically producing the elements of the bracket 12 for the virtual representation 12n of the bracket designed previously.

In this seventh step of the method, a bracket 12, for each tooth 13, is fabricated from an actual blank 50, the said blank being produced in a biocompatible material in accordance with the numerical blank selected during the fourth step of the design of the bracket 12, in the numerical process.

For example, the numerical object, representative of the final bracket, is exported in the form of numerical files to a machine tool or some other device intended to manufacture the final bracket from a biocompatible material using known methods.

In one exemplary embodiment of the seventh step, the bracket 12 is manufactured by machining. The numerical files are imported to a multi-axis machine tool in which the machining sequences are programmed. An actual blank 50 corresponding to the bracket 12 the numerical representation 50n of which was used is placed in the work zone of the machine and is then machined.

In another exemplary embodiment of this seventh step, manufacture is performed using a laser sintering technique or a grinding technique, using the exported numerical files. These techniques in particular can more easily produce the square-section or rectangular-section housings, slots, secondary slots in the bracket bonding pad or the bracket body of the bracket.

This seventh step is performed for each bracket of the orthodontic appliance.

The invention is described in the case of substantially spherical bracket bodies although this choice does not restrict the invention. Thus, other shapes of bracket body, for example rounded or blunted shapes, may also be used to improve patient comfort or display particular advantages for the production of the secondary slots. A person skilled in the art will be able to adapt this invention to suit bracket body shapes that have not been described.

The invention has been described in the preferred case of a flat orthodontic archwire, on the one hand because the forces applied by flat archwires are best suited to buccal physiology, and on the other hand because they can be produced on an industrial scale. The method according to the invention makes it possible to produce an orthodontic appliance which has no difficulty in responding to this choice of a flat archwire. However, this choice is not a limitation of the invention and a person skilled in the art will be able to adapt the invention to bended arches for orthodontic appliances intended for specific dentitions.

The brackets thus produced are tailored to form an orthodontic appliance for each patient and are customized to suit each of the patient's teeth.

The invention claimed is:

1. A method of producing a customized orthodontic appliance (1), the orthodontic appliance comprising brackets fixed to teeth of a dental arch of a patient, each bracket being fixed to a surface of a tooth of the dental arch by a bracket bonding pad of the bracket, and an orthodontic archwire fixed to the brackets in a housing of a bracket body of each bracket, the method comprising:

constructing, by a processing device, a numerical representation of each bracket from a numerical representation of the desired end-of-treatment dental arch, known as the dental arch final numerical representation, the operation of constructing the numerical representation of each bracket comprising:

positioning a numerical representation of the orthodontic archwire with respect to the dental arch final numerical representation, then for each tooth of the dental arch final numerical representation, positioning a numerical representation of a volume representative of an envelope volume of a bracket body, known as a second volume, of a bracket blank such that it interferes with the orthodontic archwire and in close proximity to the relevant tooth, and for each tooth of the dental arch final numerical representation, positioning a numerical representation of a volume representative of an envelope volume of a bracket bonding pad, known as a first volume, of the bracket blank such that it interferes with the second volume and with the volume of the relevant tooth, then, determining, for each tooth in the first volume and in the second volume, volumetric exclusion zones, which volumetric exclusion zones contain all of the volumes that interfere with the tooth for the first volume and all of the volumes that interfere with the orthodontic archwire for the second volume, wherein the numerical representation of the bracket of one tooth being determined by the volume of the bracket blank minus the volumetric exclusion zones.

2. The method according to claim 1, wherein the volumetric exclusion zones of the first volume are defined in such a way as to determine a substantially constant thickness of the numerical representation of the bracket bonding pad.

3. The method according to claim 1, wherein the blank is chosen from a database comprising at least two models of numerical representation of blanks.

4. The method according to claim 1, wherein the blank is chosen in relation to the shape of the relevant tooth so as to minimize the volume of the exclusion zones while at the same time keeping a sufficient aerial contact between a bearing surface of the bracket bonding pad and the surface of the tooth.

5. The method according to claim 1, wherein the numerical representation of the orthodontic archwire is positioned in such a way that a distance d, for each tooth of the dental arch final numerical representation, between the numerical representation of the orthodontic archwire and the surface of each tooth is greater than a minimum distance $d_{min}$ that corresponds to a minimum thickness of the numerical representation of the brackets at their bracket bodies.

6. The method according to claim 1, wherein, for each tooth of the dental arch final numerical representation, the numerical representation of the second volume is positioned in such a way that a reference point of the second volume corresponds to a point of intersection between the numerical representation of the orthodontic archwire and an orthogonal projection of a center of the relevant tooth.

7. The method according to claim 1, wherein housings are produced, for certain sectors of the dental arch, with a cross section appreciably larger than a cross section of the orthodontic archwire so that the orthodontic archwire can slide naturally along the dental arch in the housings as the teeth of the dental arch move.

8. The method according to claim 1, wherein the orthodontic appliance is produced from a flat orthodontic archwire.

9. The method according to claim 1, wherein the numerical representations of the brackets are placed on lingual surfaces of the teeth of the dental arch final numerical representation.

10. The method according to claim 1, wherein the numerical representations of the brackets are placed on vestibular surfaces of the teeth of the dental arch final numerical representation.

11. The method according to claim 1, wherein the exclusion zones of the second volume determine a housing in the form of an open slot in the numerical representation of the bracket body to accommodate the numerical representation of the orthodontic archwire and, if appropriate, a numerical representation of orthodontic archwire self-ligating means.

12. The method according to claim 1, wherein the exclusion zones of the second volume determine a housing in the form of a tube in the numerical representation of the bracket body to accommodate the numerical representation of the orthodontic archwire.

13. The method according to claim 1, wherein volumetric exclusion zones are determined in a numerical representation of at least one volume representative of an envelope volume of an ancillary accessory, known as a third volume, of the bracket blank, and are then subtracted from the blank.

14. The method according to claim 1, wherein the final numerical representation of the dental arch desired at the end of the treatment of the patient is produced from a numerical representation of the dental arch of the patient prior to treatment.

15. The method according to claim 1, wherein the brackets are produced from a biocompatible material in accordance with the numerical representations.

\* \* \* \* \*

UNITED STATES PATENT AND TRADEMARK OFFICE
CERTIFICATE OF CORRECTION

PATENT NO.       : 8,371,847 B2
APPLICATION NO.  : 12/937588
DATED            : February 12, 2013
INVENTOR(S)      : Baron et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 194 days.

Signed and Sealed this
First Day of September, 2015

Michelle K. Lee
*Director of the United States Patent and Trademark Office*